US010745582B2

(12) United States Patent
Farcet et al.

(10) Patent No.: US 10,745,582 B2
(45) Date of Patent: Aug. 18, 2020

(54) DISPERSION OF SOFT POLYMER PARTICLES, COSMETIC COMPOSITION COMPRISING IT AND COSMETIC TREATMENT METHOD

(75) Inventors: Celine Farcet, Les Pavillons sous Bois (FR); Lisa Houillot, Mannheim (DE); Maud Save, Escala (FR); Bernadette Charleux, Lyons (FR)

(73) Assignee: L'OREAL, Paris (FR)

( * ) Notice: Subject to any disclaimer, the term of this patent is extended or adjusted under 35 U.S.C. 154(b) by 410 days.

(21) Appl. No.: 13/120,437

(22) PCT Filed: Oct. 6, 2009

(86) PCT No.: PCT/EP2009/062947
§ 371 (c)(1),
(2), (4) Date: Jun. 23, 2011

(87) PCT Pub. No.: WO2010/046229
PCT Pub. Date: Apr. 29, 2010

(65) Prior Publication Data
US 2011/0243864 A1    Oct. 6, 2011

Related U.S. Application Data

(60) Provisional application No. 61/109,514, filed on Oct. 30, 2008.

(30) Foreign Application Priority Data

Oct. 24, 2008 (FR) ...................................... 08 57236

(51) Int. Cl.
| | |
|---|---|
| A61K 8/81 | (2006.01) |
| A61Q 1/06 | (2006.01) |
| A61K 8/92 | (2006.01) |
| A61Q 3/02 | (2006.01) |
| A61Q 1/12 | (2006.01) |
| A61Q 1/10 | (2006.01) |
| A61Q 19/00 | (2006.01) |
| C09D 133/26 | (2006.01) |
| C08J 3/11 | (2006.01) |
| C08F 293/00 | (2006.01) |
| A61Q 1/02 | (2006.01) |
| A61Q 1/04 | (2006.01) |
| C08F 287/00 | (2006.01) |
| C08F 279/02 | (2006.01) |
| A61K 8/04 | (2006.01) |
| A61Q 5/06 | (2006.01) |
| A61Q 17/04 | (2006.01) |
| A61Q 19/10 | (2006.01) |
| A61Q 19/04 | (2006.01) |
| A61Q 19/08 | (2006.01) |

(52) U.S. Cl.
CPC .............. *C09D 133/26* (2013.01); *A61K 8/04* (2013.01); *A61K 8/8152* (2013.01); *A61Q 1/02* (2013.01); *A61Q 1/04* (2013.01); *A61Q 1/06* (2013.01); *A61Q 1/10* (2013.01); *A61Q 1/12* (2013.01); *A61Q 3/02* (2013.01); *A61Q 19/00* (2013.01); *C08F 279/02* (2013.01); *C08F 287/00* (2013.01); *C08F 293/005* (2013.01); *C08J 3/11* (2013.01); *A61Q 5/06* (2013.01); *A61Q 5/065* (2013.01); *A61Q 17/04* (2013.01); *A61Q 19/04* (2013.01); *A61Q 19/08* (2013.01); *A61Q 19/10* (2013.01); *C08F 2438/03* (2013.01)

(58) Field of Classification Search
CPC ... A61K 8/06; A61K 8/90; A61K 8/04; A61K 8/84; A61K 8/89
USPC ................... 424/61, 70.7, 64, 63, 69, 78.03
See application file for complete search history.

(56) References Cited

U.S. PATENT DOCUMENTS

| | | | |
|---|---|---|---|
| 4,098,980 A | 7/1978 | Markle et al. | |
| 2004/0120920 A1* | 6/2004 | Lion et al. | 424/70.16 |
| 2005/0220728 A1* | 10/2005 | Kanji et al. | 424/59 |
| 2006/0147403 A1* | 7/2006 | Ferrari et al. | 424/70.16 |
| 2006/0193803 A1* | 8/2006 | Farcet | 424/70.1 |

FOREIGN PATENT DOCUMENTS

| | | |
|---|---|---|
| FR | 2 785 530 | 5/2000 |
| GB | 941305 | 11/1963 |
| WO | WO 2007/007231 | * 1/2007 |

OTHER PUBLICATIONS

Sigmaaldrich, Reference:Polymer Properites, Theremal Transitions of Homopolymers: Glass Transition & Melting Point, 2013.*
ChemYQ (poly(methyl acrylate) Material Safety Sheet, 2013.*
International Search Report dated Feb. 5, 2010 in PCT/EP09/062947 filed Oct. 6, 2009.

* cited by examiner

*Primary Examiner* — Anna R Falkowitz
(74) *Attorney, Agent, or Firm* — Oblon, McClelland, Maier & Neustadt, L.L.P.

(57) ABSTRACT

The present invention relates to a dispersion of polymer particles in a liquid carbon-based medium, the said particles having a flexible polymeric core and being surface-stabilized with a block stabilizing polymer comprising at least one block that is soluble in the said carbon-based medium and at least one block that is insoluble in the said carbon-based medium.
The invention also relates to a cosmetic composition comprising the said dispersion, and to a cosmetic treatment process using the said composition.

18 Claims, No Drawings

DISPERSION OF SOFT POLYMER PARTICLES, COSMETIC COMPOSITION COMPRISING IT AND COSMETIC TREATMENT METHOD

The present invention relates to novel cosmetic compositions comprising dispersions of polymer particles, to the said dispersions and to their use in cosmetics, especially for obtaining a glossy deposit that is pleasant to wear.

It is known practice to use in cosmetics dispersions of polymer particles, generally of nanometric size, in aqueous or organic media. Thus, European patent application EP-A-0 749 747 describes a cosmetic composition comprising a dispersion of polymer particles, in an organic medium, the said dispersion being stabilized by adding stabilizing polymers that bond non-covalently by means of physical interactions to the polymer particles. However, this type of composition has the drawback of requiring the addition to the organic medium of an amount of stabilizing polymer higher than that effectively bonded to the polymer particles, in order to obtain a relatively stable dispersion. Now, during the addition of adjuvants such as pigments, some of the stabilizing polymers have a tendency to be desorbed from the polymer particles and to associate with the said adjuvants, which contributes towards destabilizing the dispersion, especially by formation of aggregates between the polymer particles.

Cosmetic compositions comprising dispersions, in an organic medium, of acrylic polymer particles comprising a backbone that is insoluble in the said medium, and a part that is soluble in the said medium, formed from side chains covalently bonded to the said backbone, were then proposed, in order to dispense with the use of such stabilizing polymers. This is especially described in patent application EP 1 428 844. In this case, the polymer particles are stabilized by a macromonomer that is chemically bonded to the polymer particles.

However, the dispersions described in these documents, although leading to cosmetically acceptable film-forming deposits, do not make it possible to obtain optimum cosmetic properties, especially in terms of glidance, absence of tack, comfort, remanence of the composition, feel and gloss.

In particular, the films obtained from these dispersions have a certain tacky nature and sensitivity to fatty substances, especially over time.

Now, polymers that can show resistance and remanence with respect to external attack, especially "attack" by fatty substances, for instance dietary oil or sebum, while at the same time being flexible and glossy, are sought, especially in the field of makeup.

The aim of the present invention is to overcome these limitations and to propose dispersions, in oily medium, of polymer particles that make it possible to obtain good cosmetic properties such as good adhesion to the support (skin or hair), and thus good remanence of the cosmetic composition, good resistance to attack and good gloss, while at the same time being non-tacky.

One subject of the present invention is a dispersion of polymer particles in a liquid carbon-based medium, the said particles having a flexible polymeric core and being surface-stabilized with a block stabilizing polymer comprising at least one block that is soluble in the said carbon-based medium and at least one block that is insoluble in the said carbon-based medium.

Another subject of the invention is a cosmetic composition comprising, in a cosmetically acceptable medium, at least one dispersion as defined above.

The dispersions of polymer particles according to the invention have suitable cosmetic properties, and especially good remanence of the cosmetic composition, and good stability over time. The comfort of the cosmetic composition is improved, as are its feel, its softness, its glidance and its non-tacky nature. The composition makes it possible to obtain a film that is glossy and sparingly tacky, while at the same time also being sparingly brittle or non-brittle and sufficiently flexible, and advantageously showing good resistance to fatty substances.

The compositions according to the invention may provide, in the field of makeup, increased comfort properties, especially improved glidance, in particular in a humid environment. Furthermore, they may show improved resistance to external attack (oil, meals or sebum) and to friction. The comfort and remanence are thus improved.

The dispersions also show great affinity for the oily media usually used in cosmetics.

In addition, they may have a high solids content while at the same time maintaining their stability.

Moreover, these dispersions comprise a dispersant in very small amount and of nature similar to that of the polymer forming the particle; the final properties of the film, for example the Tg, will therefore be little affected or unaffected by the dispersant, unlike what may take place with the use of standard dispersants that may disrupt the final properties, especially as a result of their chemical nature and/or the larger amount used (in general at least 10%).

To achieve the aim pursued by the present invention, it was necessary to design both the core of the particle and its stabilizer, in a specifically adapted manner.

Thus, according to the present invention, it is desired to prepare "flexible" particles that will form a deposit on the keratin substrate; during drying of the dispersion, after evaporation of the organic medium, the said particles may coalesce and form a film.

Furthermore, the medium of the dispersion may be a liquid carbon-based medium.

It has been found that the particular choice of monomers capable of forming the particles according to the invention, and the particular choice of the liquid carbon-based medium, could also make it possible to obtain a stable dispersion capable of comprising the particles in large amount, leading to a dispersion with a high solids content.

In order to obtain such a dispersion, it is proposed to polymerize particular monomers, which are capable of forming the "flexible" polymeric core of the particle, in the presence of a block stabilizing polymer comprising at least one block that is soluble and at least one block that is insoluble in the dispersion medium, the said stabilizer partly forming the "hair" of the particle.

As mentioned above, to obtain a flexible film-forming deposit that is comfortable to wear and also glossy, the particles in dispersion, and more particularly the core of the said particles, is/are preferably flexible.

Preferably, the said particles are not, or are sparingly, crosslinked, so as to conserve their film-forming nature.

The said particles with a flexible polymeric core may be obtained by polymerization of monomers, alone or as a mixture, chosen such that the glass transition temperature (Tg) of the resulting polymer, forming the flexible core, is strictly less than 20° C.

In the present invention, the Tg (or glass transition temperature) values indicated are theoretical Tg values determined from the theoretical Tg values of the constituent monomers of the polymer, which may be found in a reference manual, such as the Polymer Handbook, 4th edition (Brandrup, Immergut, Grulke), 1999, John Wiley. The Tg of a polymer may be determined according to the following relationship, known as Fox's law:

$$\frac{1}{Tg} = \sum_i \left(\frac{\varpi i}{Tgi}\right)$$

wi being the mass fraction of the monomer i in the polymer and Tgi being the glass transition temperature of the homopolymer of the monomer i (expressed in Kelvins).

In the present description, the term "monomer with a Tg" means the monomer whose homopolymer has such a glass transition temperature.

In order to obtain particles with a flexible polymeric core, whose Tg is strictly less than 20° C., it is possible to polymerize 60% to 99.9% by weight, relative to the total weight of monomers, of monomers whose homopolymer has a Tg strictly less than 20° C., especially 80-95% by weight of monomers with a Tg strictly less than 20° C.; preferentially 100% by weight of the monomers capable of forming the core of the particle have a Tg strictly less than 20° C. The monomers whose homopolymer has a Tg of greater than or equal to 20° C. (monomers with a Tg of greater than or equal to 20° C.) may thus be present to form the core of the particle, but in a minor amount, i.e. between 0.1% and 40% by weight and especially 5% to 20% by weight relative to the total weight of monomers serving to form the core of the particle.

The polymer capable of forming the polymeric core of the particle may be obtained by conventional radical polymerization or controlled radical polymerization (CRP), especially in a liquid carbon-based medium; the latter technique is perfectly suitable for use since it makes it possible to control the size of the particles in these media and their dispersity.

Preferably, the monomers capable of forming the polymeric core of the particle are chosen from monomers that are insoluble in the liquid carbon-based medium of the dispersion.

In the present description, the term "insoluble monomer" means any monomer whose homopolymer is insoluble, at 5% by weight, at 20° C., in the liquid carbon-based medium of the dispersion; the monomer per se possibly being soluble or insoluble in the said medium.

The insoluble monomers especially represent 55% to 100% by weight, in particular 65% to 95% by weight or even 70% to 85% by weight, relative to the total weight of monomers forming the polymeric core of the particle. As monomers with a Tg strictly less than 20° C., which may be used to form the polymeric core of the particle, mention may be made, alone or as a mixture, of the following monomers, and also salts thereof:

the (meth)acrylates of formula $CH_2=C(CH_3)-COOR$ or $CH_2=CH-COOR$, in which R represents a linear, branched or cyclic, saturated or unsaturated, or even aromatic, alkyl group, comprising 1 to 32 carbon atoms, which may include one or more substituents chosen from —OH, halogen atoms (F, Cl, Br and I) and —NR'R" with R' and R", which may be identical or different, chosen from linear or branched C1-C4 alkyls; and/or interrupted with an oxygen atom;

ethylenic monomers whose ester group contains silanes, silsesquioxanes, siloxanes or carbosiloxane dendrimers as described in patent EP 0 963 751, with the exception of monomers containing only one silicon atom such as methacryloxypropyltrimethoxysilane.

Among the monomers with a Tg strictly less than 20° C. that are more particularly preferred, mention may be made of:

perfluorooctyl, butyl, isobutyl, methyl, methoxyethyl, cyclohexyl or 2-ethoxyethyl acrylate;

dimethylaminoethyl or 2-ethoxyethyl methacrylate;

(meth)acryloxypropyltris(trimethylsiloxy)silane, 3-(meth)acryloxypropyl-bis(trimethylsiloxy)methylsilane, (meth)acryloxymethyltris(trimethylsiloxy)silane or (meth)acryloxymethylbis(trimethylsiloxy)methylsilane.

As monomers with a Tg of greater than or equal to 20° C., which may be used to form part of the core of the particle, mention may be made, alone or as a mixture, of the following monomers, and also salts thereof:

(i) the (meth)acrylates of formula $CH_2=C(CH_3)-COOR$ or $CH_2=CH-COOR$, in which R represents a linear, branched or cyclic, saturated or unsaturated, or even aromatic, alkyl group, comprising 1 to 32 carbon atoms, which may comprise one or more substituents chosen from —OH, halogen atoms (F, Cl, Br or I) and —NR'R" with R' and R", which may be identical or different, chosen from linear or branched C1-C4 alkyls; and especially:

methyl, ethyl, cyclohexyl, isobutyl, butyl, tert-butyl, tetrahydrofurfuryl, dicyclopentenyloxyethyl or benzyl methacrylate;

tert-butyl acrylate, trifluoroethanol methacrylate (TRIFEMA), 2-hydroxyethyl, 2-hydroxypropyl or dicyclopentenyl (meth)acrylates, (ii) the (meth)acrylamides of formula $CH_2=C(CH_3)-CONR'_3R'_4$ or $CH_2=CH-CONR'_3R'_4$ in which:

$R'_3$ and $R'_4$, which may be identical or different, represent a hydrogen atom or a linear or branched alkyl group containing from 1 to 6 carbon atoms, which may include one or more substituents chosen from —OH, =O, halogen atoms (F, Cl, Br or I) and —NR'R" with R' and R", which may be identical or different, chosen from linear or branched C1-C4 alkyls; or $R'_3$ represents a hydrogen atom and $R'_4$ represents a 1,1-dimethyl-3-oxobutyl group;

As examples of alkyl groups that can constitute $R'_3$ and $R'_4$, mention may be made of n-butyl, t-butyl, n-propyl, dimethylaminoethyl, diethylaminoethyl and dimethylaminopropyl.

Monomers that may be mentioned include dimethylaminopropylmethacrylamide, acrylamide, methacrylamide, N-tert-butylacrylamide and diacetoneacrylamide of formula $CH_2=CH-C(O)NHC(CH_3)_2-CH_2-C(O)CH_3$;

(iii) ethylenically unsaturated monomers comprising at least one carboxylic, phosphoric or sulfonic acid function, such as crotonic acid, maleic anhydride, itaconic acid, fumaric acid, maleic acid, styrenesulfonic acid, vinylbenzoic acid, vinylphosphoric acid, acrylic acid, methacrylic acid, acrylamidopropanesulfonic acid or acrylamidoglycolic acid, and salts thereof;

(iv) vinyl esters of formula $R'_6-COO-CH=CH_2$ in which $R'_6$ represents a linear or branched alkyl group comprising from 1 to 6 atoms, or a cyclic alkyl group comprising from 3 to 6 carbon atoms and/or an aromatic group, for example of benzene, anthracene or naphthalene type;

(v) ethylenically unsaturated monomers comprising at least one tertiary amine function, such as 2-vinylpyridine or 4-vinylpyridine, and mixtures thereof;

(vi) styrene and derivatives thereof.

Among the monomers with a Tg of greater than or equal to 20° C. that are more particularly preferred, mention may be made of methacrylic acid or acrylic acid; methyl, ethyl, cyclohexyl, isobutyl, butyl, tert-butyl, tetrahydrofurfuryl, dicyclopentenyloxyethyl or benzyl methacrylate; tert-butyl acrylate; trifluoroethanol methacrylate; 2-hydroxyethyl, 2-hydroxypropyl or dicyclopentenyl (meth)acrylates; dimethylaminopropylmethacrylamide; styrene and derivatives thereof, or vinyl acetate; and mixtures thereof.

One characteristic of the present invention is that the polymerization of the monomers forming the core of the particle is performed in the presence of a block stabilizing polymer, which leads to surface stabilization of the said particles by the said stabilizing polymer.

The said block stabilizing polymer is preferably a copolymer as described in patent application EP 1 704 854. It comprises at least a first block that is soluble in the liquid carbon-based medium of the dispersion and at least a second block that is insoluble in the said medium.

In the present invention, the term "block" means a polymer sequence, formed from several monomers, especially from at least 5 monomers, which may be identical or different, and which may thus be in the form of a homopolymer or a random, alternating, gradient or block, especially diblock, triblock or multiblock, copolymer. Preferably, the block is of homopolymer or gradient type, preferentially a homopolymer. For each block, the choice of monomers and of their amount, and also the architecture of the block, may be made by a person skilled in the art on the basis of his general knowledge so as finally to obtain a block having the required solubility (soluble or insoluble) in the carbon-based medium under consideration. Each block may have an identical or different length, molar mass, chemical nature and/or architecture. The term "soluble" means that the block is completely dissolved (with no apparent insoluble deposit, aggregate or sediment), visually, at 20° C., at a concentration of greater than or equal to 5% by weight, in the carbon-based medium under consideration.

The block stabilizing polymer is preferably of the "triblock" type, i.e. it comprises three blocks, and is especially of the soluble/insoluble/soluble triblock type; however, it may be of the "diblock" type of the soluble/insoluble type, or even of "multiblock" type (more than three blocks).

Preferably, the block stabilizing polymer is linear; however, it may be grafted and/or branched. The term "linear" refers to a polymer for which there is no voluntary addition, during its polymerization, of a compound whose purpose is to crosslink and/or branch it.

Preferably, the block stabilizing polymer has a number-average molecular weight (Mn) of between 1000 and 700 000, especially between 5000 and 500 000 and better still between 10 000 and 350 000, or even between 15 000 and 150 000.

Preferably, it has a mass polydispersity index (Ip) of less than or equal to 6, preferably between 1.05 and 4, especially between 1.1 and 3, or even between 1.15 and 2.5. The mass polydispersity index (Ip) is equal to the ratio of the weight-average molecular mass (Mw) to the number-average molecular mass (Mn). The weight-average (Mw) and number-average (Mn) molecular masses are determined by gel permeation liquid chromatography (GPC), eluting with THF, the calibration curve being established with linear polystyrene standards, using a refractometric detector or a light-scattering detector.

The block stabilizing polymer comprises a first block that is soluble in the carbon-based dispersion medium and at least a second block, which is insoluble in the said medium.

The soluble block preferably comprises 50% to 100% by weight of monomer that is soluble in the said medium, especially from 60% to 90% by weight and better still from 70% to 80% by weight of soluble monomer, alone or as a mixture. It may thus also comprise 0 to 50% by weight, especially from 10% to 40% by weight, or even from 20% to 30% by weight of monomer that is insoluble in the said medium, alone or as a mixture.

Similarly, the insoluble block preferably comprises 50% to 100% by weight of monomer that is insoluble in the said medium, especially from 60% to 90% by weight and better still from 70% to 80% by weight of insoluble monomer, alone or as a mixture. It may also comprise 0 to 50% by weight, especially from 10% to 40% by weight, or even from 20% to 30% by weight of monomer that is soluble in the said medium, alone or as a mixture.

The term "monomer that is soluble in the medium" means any monomer whose homopolymer is in soluble form, i.e. fully dissolved at a concentration of greater than or equal to 5% by weight at room temperature (20° C.) in the said medium.

The term "insoluble monomer" thus means any monomer whose homopolymer is not in soluble form, i.e. completely dissolved at a concentration of greater than or equal to 5% by weight at room temperature (20° C.) in the said medium. However, the "insoluble" monomers may, as monomers, be soluble in the medium under consideration, it being understood that they become insoluble after polymerization.

As soluble monomers that may be used to form all or part of the soluble block, mention may be made, alone or as a mixture, of the following monomers:

the methacrylates of formula $CH_2=C(CH_3)-COOR_1$ in which $R_1$ represents a linear or branched C8-C22 alkyl group such as lauryl, behenyl or stearyl; or alternatively a cyclic alkyl group containing 8 to 30 carbon atoms, such as isobornyl; or alternatively $R_1$ represents a tert-butyl group;

the acrylates of formula $CH_2=CH-COOR_2$ in which $R_2$ represents a linear or branched C8-C22 alkyl group such as lauryl, behenyl, stearyl or 2-ethylhexyl; or alternatively a cyclic alkyl group containing 8 to 30 carbon atoms, such as isobornyl; or alternatively $R_2$ represents an isobutyl group;

the (meth)acrylamides of formula $CH_2=C(CH_3)-CONR_3R_4$ or $CH_2=CH-CONR_3R_4$, in which $R_3$ represents a hydrogen atom or a linear or branched C1-C12 alkyl group and $R_4$ represents a linear or branched $C_8$ to $C_{12}$ alkyl group, such as an isooctyl, isononyl or undecyl group;

the di-n-alkylitaconates of formula $CH_2=C(CH_2-COO(CH_2)_{n-1}-CH_3)-COO(CH_2)_{n-1}-CH_3$, with n being an integer greater than or equal to 5, especially from 5 to 12;

the vinyl esters of formula $R_5-CO-O-CH=CH_2$ in which $R_5$ represents a linear or branched $C_8$ to $C_{22}$ alkyl group;

the ethers of vinyl alcohol and of an alcohol of formula $R_6O-CH=CH_2$ in which $R_6$ represents a linear or branched alkyl group containing from 8 to 22 carbon atoms;

ethylenic monomers in which the ester group contains silanes or siloxanes, and which contain only one silicon atom, such as (meth)acryloxypropyl-trimethoxysilane;

carbon-based macromonomers with a polymerizable end group.

The term "macromonomer with a polymerizable end group" means any oligomer comprising on only one of its ends a polymerizable end group capable of reacting during the polymerization reaction with ethylenic monomers. The polymerizable group of the macromonomer may advantageously be an ethylenically unsaturated group capable of undergoing free-radical polymerization. The said polymerizable end group may be in particular a vinyl or (meth) acrylate (or (meth)acryloxy) group and preferably a (meth) acrylate group. The term "carbon-based macromonomer" means a non-silicone macromonomer, and especially an oligomeric macromonomer obtained by polymerization of non-silicone ethylenically unsaturated monomer(s), and mainly by polymerization of acrylic monomers and/or non-acrylic vinyl monomers.

As carbon-based macromonomers bearing a polymerizable end group, mention may be made in particular of:

(i) linear or branched C6-C22 and preferably C8-C18 alkyl (meth)acrylate homopolymers and copolymers, containing a polymerizable end group chosen from vinyl or (meth)acrylate groups, among which mention may be made in particular of: poly(2-ethylhexyl acrylate) macromonomers containing mono(meth)acrylate end groups; poly(dodecyl acrylate) or poly(dodecyl methacrylate) macromonomers containing mono(meth) acrylate end groups; poly(stearyl acrylate) or poly (stearyl methacrylate) macromonomers containing mono(meth)acrylate end groups.

Such macromonomers are especially described in patents EP 895 467 and EP 96459 and in the article Gillman, Polymer Letters, Vol. 5, pages 477-481 (1967).

Mention may be made in particular of macromonomers based on poly(2-ethylhexyl acrylate) or poly(dodecyl acrylate) containing mono(meth)acrylate end groups.

(ii) polyolefins with an ethylenically unsaturated end group, in particular those with a (meth)acrylate end group. Examples of such polyolefins that may be mentioned in particular include the following macromonomers, it being understood that they contain a (meth) acrylate end group: polyethylene macromonomers, polypropylene macromonomers, macromonomers of polyethylene/polypropylene copolymer, macromonomers of polyethylene/polybutylene copolymer, polyisobutylene macromonomers, polybutadiene macromonomers; polyisoprene macromonomers; polybutadiene macromonomers; poly(ethylene/butylene)-polyisoprene macromonomers.

Such macromonomers are described in particular in EP 1 347 013 or in U.S. Pat. No. 5,625,005, which mentions ethylene/butylene and ethylene/propylene macromonomers containing a (meth)acrylate reactive end group. Mention may be made in particular of poly(ethylene/butylene) methacrylate, such as the product sold under the name Kraton Liquid L-1253 by Kraton Polymers.

Particularly preferred soluble monomers that may be mentioned, alone or as a mixture, include:

the methacrylates of formula $CH_2=C(CH_3)-COOR_1$ in which $R_1$ represents a linear or branched C8-C22 alkyl group such as lauryl, behenyl or stearyl; or alternatively a cyclic alkyl group containing from 8 to 30 carbon atoms, such as isobornyl; or alternatively $R_1$ represents a tert-butyl group;

the acrylates of formula $CH_2=CH-COOR_2$ in which $R_2$ represents a linear or branched C8-C22 alkyl group such as lauryl, behenyl, 2-ethylhexyl or stearyl; or alternatively a cyclic alkyl group containing from 8 to 30 carbon atoms, such as isobornyl; or alternatively $R_2$ represents an isobutyl group.

Mention may thus be made of 2-ethylhexyl acrylate, isobornyl (meth)acrylate, lauryl (meth)acrylate, stearyl (meth)acrylate, behenyl (meth)acrylate, isobutyl acrylate and tert-butyl methacrylate, and mixtures thereof.

As insoluble monomers that may be used, especially to form all or part of the insoluble block, mention may be made, alone or as a mixture, of the following monomers, and also the salts and mixtures thereof:

(i) the (meth)acrylates of formula: $CH_2=C(CH_3)-COOR'_1$ or $CH_2=CH-COOR'_1$ in which $R'_1$ represents a group chosen from:

a linear or branched alkyl group containing from 1 to 6 carbon atoms, the said group possibly comprising in its chain one or more heteroatoms chosen from O, N and S; and/or possibly comprising one or more substituents chosen from —OH, halogen atoms (F, Cl, Br or I) and —NR'R" with R' and R", which may be identical or different, chosen from linear or branched C1-C4 alkyls; and/or possibly being substituted with at least one polyoxyalkylene group, in particular with a C2-C4 alkylene and especially a polyoxyethylene and/or a polyoxypropylene, the said polyoxyalkylene group consisting of a repetition of from 5 to 30 oxyalkylene units; tert-butyl methacrylate and isobutyl acrylate are excluded from this definition;

a cyclic alkyl group containing from 3 to 6 carbon atoms, the said group possibly comprising in its chain one or more heteroatoms chosen from O, N and S and/or possibly comprising one or more substituents chosen from OH and halogen atoms (F, Cl, Br or I);

Examples of $R'_1$ that may be mentioned include methyl, ethyl, propyl, butyl, methoxyethyl, ethoxyethyl, methoxypolyoxyethylene 30, trifluoroethyl, 2-hydroxyethyl, 2-hydroxypropyl, dimethylaminoethyl, diethylaminoethyl and dimethylaminopropyl groups;

(ii) the (meth)acrylamides of formula: $CH_2=C(CH_3)-CONR'_3R'_4$ or $CH_2=CH-CONR'_3R'_4$, in which:

$R'_3$ and $R'_4$, which may be identical or different, represent a hydrogen atom or a linear or branched alkyl group containing from 1 to 6 carbon atoms, possibly comprising one or more substituents chosen from —OH, halogen atoms (F, Cl, Br or I) and —NR'R" with R' and R", which may be identical or different, chosen from linear or branched C1-C4 alkyls; or $R'_3$ represents a hydrogen atom and $R'_4$ represents a 1,1-dimethyl-3-oxobutyl group;

As examples of alkyl groups that can constitute $R'_3$ and $R'_4$, mention may be made of n-butyl, t-butyl, n-propyl, dimethylaminoethyl, diethylaminoethyl and dimethylaminopropyl;

(iii) ethylenically unsaturated monomer(s) comprising at least one carboxylic, phosphoric or sulfonic acid function, such as crotonic acid, maleic anhydride, itaconic acid, fumaric acid, maleic acid, styrenesulfonic acid, vinylbenzoic acid, vinylphosphoric acid, acrylic acid, methacrylic acid and acrylamidopropanesulfonic acid, and salts thereof;

(iv) the vinyl esters of formula $R'_6-COO-CH=CH_2$ in which $R'_6$ represents a linear or branched alkyl group containing from 1 to 6 atoms or a cyclic alkyl group containing from 3 to 6 carbon atoms and/or an aromatic group, for example of benzene, anthracene or naphthalene type;

(v) ethylenically unsaturated monomers comprising at least one tertiary amine function, such as 2-vinylpyridine or 4-vinylpyridine, and mixtures thereof;

(vi) the di-n-alkylitaconates of formula $CH_2=C(CH_2-COO(CH_2)_{n-1}-CH_3)-COO(CH_2)_{n-1}-CH_3$, with n being an integer from 0 to 4;

(vii) ethylenic monomers in which the ester group contains silanes, silsesquioxanes, siloxanes or carbosiloxane dendrimers as described in patent EP 0 963 751, with the exception of monomers containing only one silicon atom such as methacryloxypropyl trimethoxysilane. Preferred monomers are (meth)acryloxypropyltris(trimethylsiloxy)silane, (meth)acryloxypropylbis(trimethylsiloxy)methylsilane, (meth)acryloxymethyltris(trimethylsiloxy)silane and (meth)acryloxymethylbis(trimethylsiloxy)methylsilane;

(viii) PDMS macromonomers, such as polydimethylsiloxanes containing monoacryloyloxy or monomethacryloyloxy end group, and especially those having the following formula:

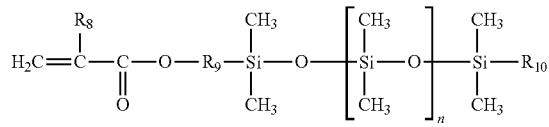

in which:

$R_8$ denotes a hydrogen atom or a methyl group; preferably methyl;

$R_9$ denotes a linear or branched, preferably linear, divalent hydrocarbon-based group containing from 1 to carbon atoms and optionally containing one or two ether bonds —O—; preferably ethylene, propylene or butylene;

$R_{10}$ denotes a linear or branched alkyl group containing from 1 to 10 carbon atoms and especially from 2 to 8 carbon atoms; preferably methyl, ethyl, propyl, butyl or pentyl;

n denotes an integer ranging from 1 to 300, preferably ranging from 3 to 200 and preferentially ranging from 5 to 100.

Monomethacryloyloxypropyl polydimethylsiloxanes such as those sold under the name PS560-K6 by UCT (United Chemical Technologies Inc.) or under the name MCR-M17 by Gelest Inc. may be used in particular.

Among the salts, mention may be made of those obtained by neutralization of acidic groups using mineral bases such as sodium hydroxide, potassium hydroxide or ammonium hydroxide, or organic bases such as alkanolamines, for instance monoethanolamine, diethanolamine, triethanolamine or 2-methyl-2-amino-1-propanol. Mention may also be made of the salts formed by neutralization of the tertiary amine units, for example using a mineral or organic acid. Among the mineral acids that may be mentioned are sulfuric acid, hydrochloric acid, hydrobromic acid, hydriodic acid, phosphoric acid and boric acid. Among the organic acids that may be mentioned are acids comprising one or more carboxylic, sulfonic or phosphonic groups. These may be linear, branched or cyclic aliphatic acids or alternatively aromatic acids. These acids may also comprise one or more heteroatoms chosen from O and N, for example in the form of hydroxyl groups. Mention may be made especially of acetic acid, propionic acid and terephthalic acid, and also citric acid and tartaric acid.

Particularly preferred insoluble monomers that may be mentioned include:

the (meth)acrylates of formula: $CH_2 = C(CH_3) - COOR'_1$ or $CH_2 = CH - COOR'_1$ and in particular methyl, ethyl, propyl or butyl (meth)acrylate; isobutyl methacrylate; methoxy ethyl or ethoxy ethyl (meth)acrylate; trifluoroethyl methacrylate; dimethylaminoethyl methacrylate, diethylaminoethyl methacrylate, 2-hydroxypropyl methacrylate, 2-hydroxyethyl methacrylate, 2-hydroxypropyl acrylate or 2-hydroxyethyl acrylate;

ethylenically unsaturated monomers comprising at least one carboxylic acid function, and especially (meth)acrylic acid and salts thereof;

ethylenic monomers in which the ester group contains silanes;

polydimethylsiloxanes containing a monoacryloyloxy or monomethacryloyloxy end group, having the following formula:

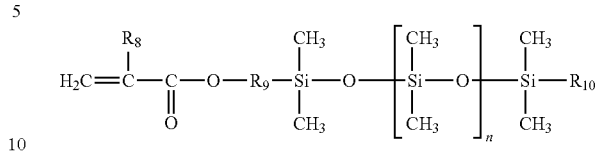

in which:

$R_8$ denotes a hydrogen atom or a methyl group; preferably methyl;

$R_9$ denotes a linear or branched, preferably linear, divalent hydrocarbon-based group containing from 1 to 10 carbon atoms and optionally containing one or two ether bonds —O—; preferably ethylene, propylene or butylene;

$R_{10}$ denotes a linear or branched alkyl group containing from 1 to 10 carbon atoms and especially from 2 to 8 carbon atoms; preferably methyl, ethyl, propyl, butyl or pentyl;

n denotes an integer ranging from 1 to 300, preferably ranging from 3 to 200 and preferentially ranging from 5 to 100.

Mention may be made more particularly of methyl (meth)acrylate, ethyl (meth)acrylate, (meth)acrylic acid, maleic anhydride, (meth)acryloxypropyl-tris(trimethylsiloxy)silane, (meth)acryloxypropylbis(trimethylsiloxy)methylsilane, (meth)acryloxymethyltris(trimethylsiloxy)silane and (meth)acryloxymethylbis(trimethylsiloxy)methylsilane.

The block stabilizing polymers that will be most particularly preferred are those in which:

(i) the soluble block comprises 50-100% by weight of monomers chosen, alone or as a mixture, from:

the methacrylates of formula $CH_2 = C(CH_3) - COOR_1$ in which $R_1$ represents a linear or branched C8-C22 alkyl group such as lauryl, behenyl or stearyl; or alternatively a cyclic alkyl group containing 8 to 30 carbon atoms, such as isobornyl; or alternatively $R_1$ represents a tert-butyl group;

the acrylates of formula $CH_2 = CH - COOR_2$ in which $R_2$ represents a linear or branched C8-C22 alkyl group such as lauryl, behenyl, 2-ethylhexyl or stearyl; or alternatively a cyclic alkyl group containing 8 to 30 carbon atoms, such as isobornyl; or alternatively $R_2$ represents an isobutyl group; and (ii) the soluble block comprises 50-100% by weight of monomers chosen, alone or as a mixture, from methyl, ethyl, propyl or butyl (meth)acrylates; isobutyl methacrylate; methoxyethyl or ethoxyethyl (meth)acrylates; trifluoroethyl methacrylate; dimethylaminoethyl methacrylate, diethylaminoethyl methacrylate, 2-hydroxypropyl methacrylate, 2-hydroxyethyl methacrylate, 2-hydroxypropyl acrylate or 2-hydroxyethyl acrylate; (meth)acrylic acid, and salts thereof.

Among the preferred stabilizing polymers, mention may be made most particularly of the following polymers: poly(2-ethylhexyl acrylate)-b-poly(methyl acrylate), poly(2-ethylhexyl acrylate)-b-poly(methyl acrylate-co-acrylic acid), poly(2-ethylhexyl acrylate-co-isobornyl acrylate)-b-poly(methyl acrylate), poly(2-ethylhexyl acrylate-co-acrylic acid)-b-poly(methyl acrylate), poly(2-ethylhexyl acrylate-co-isobornyl acrylate)-b-poly(methyl acrylate), poly(2-ethylhexyl acrylate-co-acrylic acid)-b-poly(methyl acrylate), poly(2-ethylhexyl acrylate-co-isobornyl acrylate)-b-poly(methyl acrylate-co-acrylic acid), poly(2-ethylhexyl acrylate-co-isobornyl acrylate-co-acrylic acid)-b-poly(methyl acrylate); poly(isobornyl acrylate)-b-poly(methyl acrylate), poly(isobornyl acrylate)-b-poly(methyl acrylate-co-acrylic acid); poly(isobornyl acrylate-co-acrylic acid)-b-poly (methyl acrylate), poly(isobutyl acrylate)-b-poly(methyl acrylate), poly(isobutyl acrylate)-b-poly(methyl acrylate-co-acrylic acid), poly(isobutyl acrylate-co-acrylic acid)-b-poly (methyl acrylate), poly(isobutyl acrylate-co-isobornyl acrylate)-b-poly(methyl acrylate), poly(isobutyl acrylate-co-isobornyl acrylate)-b-poly(methyl acrylate-co-acrylic acid), poly(isobutyl acrylate-co-isobornyl acrylate-co-acrylic acid)-b-poly(methyl acrylate), poly(2-ethylhexyl acrylate)-b-poly(methyl acrylate)-b-poly(2-ethylhexyl acrylate), poly (2-ethylhexyl acrylate-co-isobornyl acrylate)-b-poly(methyl acrylate)-b-poly(2-ethylhexyl acrylate-co-isobornyl acrylate), poly(2-ethylhexyl acrylate-co-acrylic acid)-b-poly (methyl acrylate)-b-poly(2-ethylhexyl acrylate-co-acrylic acid), poly(2-ethylhexyl acrylate)-b-poly(methyl acrylate-co-acrylic acid)-b-poly(2-ethylhexyl acrylate), poly(2-ethylhexyl acrylate-co-isobornyl acrylate-co-acrylic acid)-b-poly (methyl acrylate)-b-poly(2-ethylhexyl acrylate-co-isobornyl acrylate-co-acrylic acid), poly(2-ethylhexyl acrylate-co-isobornyl acrylate)-b-poly(methyl acrylate-co-acrylic acid)-b-poly(2-ethylhexyl acrylate-co-isobornyl acrylate).

The stabilizing polymer according to the invention may be prepared by a person skilled in the art according to any known polymerization technique; preferably, the first block is prepared by controlled radical polymerization (CRP), and the second block may also be prepared by CRP or by conventional polymerization.

The dispersion of polymer particles according to the invention also comprises a liquid carbon-based medium in which the said particles are dispersed.

The term "liquid medium" especially means a medium preferably having a viscosity of less than or equal to 7000 centipoises at 20° C.

According to the invention, the medium is said to be "carbon-based" if it comprises at least 50% by weight, especially from 50% to 100% by weight, for example from 60% to 99% by weight, or alternatively from 65% to 95% by weight, or even from 70% to 90% by weight, relative to the total weight of the carbon-based medium, of a carbon-based compound that is liquid at 25° C., with a global solubility parameter in the Hansen solubility space of less than or equal to 20 $(MPa)^{1/2}$, or a mixture of such compounds.

The global solubility parameter δ in the Hansen solubility space is defined in the article "Solubility parameter values" by Grulke, in the book "Polymer Handbook", 3rd Edition, Chapter VII, p. 519-559, by the relationship:

$$\delta = (d_D^2 + d_P^2 + d_H^2)^{1/2}$$

in which $d_D$ characterizes the London dispersion forces arising from the formation of dipoles induced during molecular impacts, $d_P$ characterizes the Debye interaction forces between permanent dipoles, and $d_H$ characterizes the forces of specific interactions (such as hydrogen bonding, acid/base, donor/acceptor, etc.).

The definition of solvents in the Hansen three-dimensional solubility space is described in the article by Hansen: "The three-dimensional solubility parameters", J. Paint Technol. 39, 105 (1967).

Among the liquid carbon-based compounds with a global solubility parameter in the Hansen solubility space of less than or equal to 20 $(MPa)^{1/2}$, mention may be made of liquid fatty substances, especially oils, which may be chosen from natural or synthetic, carbon-based, hydrocarbon-based, optionally fluoro oils, which are optionally branched, alone or as a mixture.

Mention may be made in particular of:

plant oils formed from fatty acid esters of polyols, in particular triglycerides, such as sunflower oil, sesame oil, rapeseed oil, macadamia oil, soybean oil, sweet almond oil, beauty-leaf oil, palm oil, grapeseed oil, corn oil, arara oil, cottonseed oil, apricot oil, avocado oil, jojoba oil, olive oil or cereal germ oil;

linear, branched or cyclic esters containing more than 6 carbon atoms, especially 6 to 30 carbon atoms; and especially isononyl isononanoate; and more particularly the esters of formula RCOOR' in which R represents a higher fatty acid residue comprising from 7 to 19 carbon atoms and R' represents a hydrocarbon-based chain comprising from 3 to 20 carbon atoms, such as palmitates, adipates, myristates and benzoates, especially diisopropyl adipate and isopropyl myristate;

hydrocarbons and especially volatile or non-volatile, linear, branched and/or cyclic alkanes, such as optionally volatile $C_5$-$C_{60}$ isoparaffins such as isododecane, Parleam (hydrogenated polyisobutene), isohexadecane, cyclohexane, or Isopars; or alternatively liquid paraffin, liquid petroleum jelly or hydrogenated polyisobutylene;

ethers containing 6 to 30 carbon atoms;

ketones containing 6 to 30 carbon atoms;

aliphatic fatty monoalcohols containing 6 to 30 carbon atoms, the hydrocarbon-based chain not comprising any substitution groups, such as oleyl alcohol, decanol, dodecanol, octadecanol, octyldodecanol and linoleyl alcohol;

polyols containing 6 to 30 carbon atoms, such as hexylene glycol;

mixtures thereof.

Preferably, the dispersion comprises, in the carbon-based medium, at least one carbon-based compound chosen from:

plant oils formed from fatty acid esters of polyols, in particular triglycerides, esters of formula RCOOR' in which R represents a higher fatty acid residue comprising 7 to 19 carbon atoms and R' represents a hydrocarbon-based chain comprising from 3 to 20 carbon atoms, volatile or non-volatile, linear or branched C8-C60 alkanes, volatile or non-volatile, cyclic, non-aromatic C5-C12 alkanes, ethers containing 7 to 30 carbon atoms, ketones containing 8 to 30 carbon atoms, aliphatic fatty monoalcohols containing 12 to 30 carbon atoms, the hydrocarbon-based chain not comprising any substitution groups, mixtures thereof.

Preferentially, the carbon-based medium comprises, as carbon-based compound, at least isopropyl myristate, octyldodecanol, C5-C60 isoparaffins, isododecane, isohexadecane, isononyl isononanoate, Parleam.

The carbon-based medium may optionally comprise additional liquid compounds that may be present in an amount strictly less than 50% by weight, especially from 1% to 40% by weight, or even from 5% to 35% by weight, or alternatively from 10% to 30% by weight, relative to the total weight of the carbon-based medium, and chosen, alone or as a mixture, from:

volatile or non-volatile silicone oils, alone or as a mixture;

Mention may be made especially of polydimethylsiloxanes and polymethylphenylsiloxanes, optionally substituted with optionally fluorinated aliphatic and/or aromatic groups, and/or comprising functional groups such as hydroxyl oil, thiol and/or amine groups; and volatile silicones, which are especially cyclic or linear, such as cyclodimethylsiloxanes, cyclophenylmethylsiloxanes and linear dimethylsiloxanes, among which mention may be made of linear dodecamethylpentasiloxane (L5), octamethylcyclotetrasiloxane, decamethylcyclopentasiloxane, hexadecamethylcyclohexasiloxane, heptamethylhexyltrisiloxane and heptamethyloctyltrisiloxane;

esters containing 2 to 5 carbon atoms, ethers containing 2 to 6 carbon atoms, ketones containing 1 to 5 carbon atoms or monoalcohols containing 1 to 5 carbon atoms.

However, according to one particular embodiment of the invention, the carbon-based medium does not contain any additional liquid compounds.

The choice of carbon-based medium may be readily made by a person skilled in the art as a function of the nature of the monomers constituting the polymer and/or of the intended use of the composition.

The dispersion of polymer particles, stabilized with a block stabilizing polymer, may be prepared according to any method that may be envisaged by a person skilled in the art, on the basis of his general knowledge.

In one particular preparation method, the block stabilizing polymer is prepared, in a first step, in dispersion form or in dry form, and the polymer particles are then synthesized, in a second step, in the presence of the said stabilizing polymer. During its synthesis, the said block stabilizing polymer, dispersed in the medium, may become spontaneously organized and form self-dispersed polymeric micelles, in stable dispersion in the medium. These micelles (or micellar particles) preferably have a size of between 5 and 500 nm, especially between 10 and 400 nm, better still from 20 to 200 nm, or even from 30 to 100 nm. Preferably, they are all the same size.

Preferentially, a dispersion of the block stabilizing polymer is prepared in the carbon-based medium desired for the final dispersion, and polymerization of the monomers capable of forming the core of the particle is performed, in the presence of this dispersion. The final size of the particles is preferably greater than 100 nm, and they are preferably all the same size.

The block stabilizing polymer, especially in dispersion, may be prepared by controlled radical polymerization or by living polymerization, especially via techniques known as nitroxide/alkoxyamine, ATRP, with organocobalt, RAFT/MADIX, degenerative transfer, TERP (tellurium), with selenium, by Iniferter, or via any living polymerization process (anionic or cationic), by metallocene, by ROMP (ring-opening metathesis polymerization), by cationic or anionic ROP (ring-opening polymerization), by GTP (group transfer polymerization), with tetraphenylethane derivatives or with diphenylethylene. The techniques used for the formation of each block may be identical or different.

A typical process may consist in preparing the first block, known as the soluble block, in the carbon-based medium of the dispersion, by polymerization of the monomer(s), a control agent and an initiator, if necessary. Next, the monomer(s) of the "insoluble" block are added in the presence or absence of initiator. The reaction temperature is preferably between −30 and 200° C., preferably from 0 to 160° C. and more preferentially from 40 to 140° C. Additional blocks may be polymerized according to the same process. For each of the blocks, the monomer(s) may be added simultaneously, in batch mode, semi-continuously or consecutively. Multi-block polymers will then be obtained. If the first block, known as the soluble block, is synthesized in bulk, the "insoluble" block may then be synthesized in bulk or in solution. The solvent may be a carbon-based solvent, which leads at the end of synthesis of the copolymer to a dispersion in the carbon-based medium. The solvent used may also be a solvent common to all the blocks; in this case, the subsequent addition of a carbon-based solvent and the optional removal of the common solvent will lead to the optional dispersion. If all the copolymer is synthesized in bulk, the addition of a carbon-based solvent will lead to the optional dispersion. If all the blocks are synthesized in solution, in a common solvent, the subsequent addition of a carbon-based solvent and the optional removal of the common solvent will lead to the optional dispersion. It is also possible at this stage to remove the common solvent so as to recover the polymer alone in order to use it in this native form or to disperse it in a carbon-based solvent so as to obtain a dispersion. Finally, if all the blocks are synthesized directly in a carbon-based solvent, the dispersion is obtained directly, in a single step. Preferably, the first block of the stabilizing polymer is prepared by controlled radical polymerization (CRP), the second block also possibly being prepared by CRP or by conventional polymerization.

The polymerization initiator may be any initiator known to those skilled in the art for radical polymerization (peroxides, azo compounds, redox couple, photochemical). In the case of certain controlled radical polymerization techniques, the same compound may act as polymerization initiator and as control agent, as is the case for alkoxyamines. For non-radical polymerizations, i.e. ionic (anionic or cationic), a person skilled in art may select the appropriate initiator.

Irrespective of the method for preparing the stabilizing polymer, block stabilizing polymers that become self-organized when they are in dispersion in the medium under consideration are finally obtained. They are composed of at least one soluble block and of at least one insoluble block, which will bring about self-organization of the polymer chains so as to form micelles having the soluble blocks at the interface with the medium and the insoluble blocks in the core of the micelle.

In a second step, the monomers capable of forming the core of the particle may be polymerized, in the presence of the said stabilizing polymer. Without being bound by the present explanation, it may be considered that the stabilizing polymer micelles will be adsorbed onto the polymer particles undergoing formation; the said monomers will in particular polymerize in the core of the said micelles and make them grow, and finally lead to very monodisperse flexible particles, with a diameter preferentially greater than 100 nm. This second step may be a conventional polymerization or a controlled radical polymerization.

In another method for preparing the dispersion according to the invention, which is a most particularly preferred method, the polymer particles in dispersion may be synthesized in a single step, with in situ synthesis of the block stabilizing polymer. The stabilizing polymer and the core of the particles are thus formed at the same time. In this case also, it may be considered that the monomers of the core of the particle will preferably polymerize at the core of the micelles undergoing formation, so as finally to lead to very monodisperse flexible particles, preferentially with a diameter greater than 100 nm. In this preparation method, the polymerization is preferably controlled radical polymerization.

In this preparation method, at least one of the blocks of the block stabilizing polymer, preferably the insoluble block, is of identical chemical nature to the core of the particle, i.e.

comprising the same monomers; it may be thought that this is due to the concomitant formation of the insoluble block of the block stabilizing polymer and of the core of the particle.

The two methods described above, for the formation of the particles in dispersion according to the invention, may be represented schematically as follows:

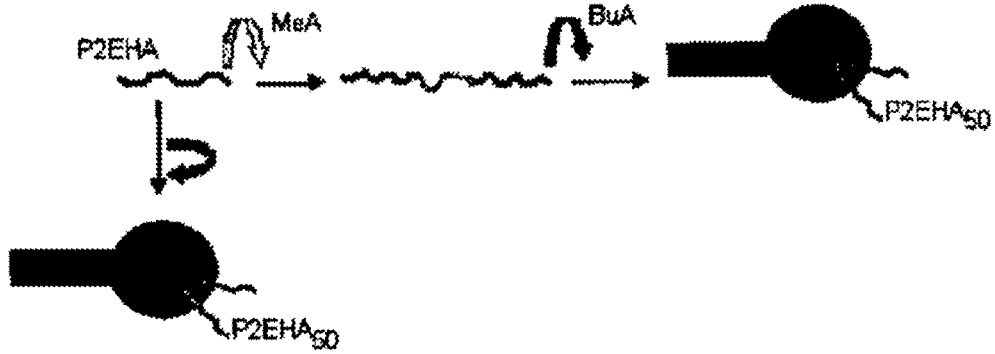

In the first method (horizontal arrow) according to this example, a first soluble poly(2-ethylhexyl acrylate) (P2EHA) block is first formed, followed by a poly(2-ethylhexyl acrylate)-b-polymethyl acrylate-b-poly(2-ethylhexyl acrylate) triblock polymer; butyl acrylate (BuA) is then polymerized in the presence of the triblock, which has previously become organized as micelles, and a flexible poly(butyl acrylate) particle stabilized by the said triblock is finally obtained.

In the second method (vertical arrow) according to this example, a first flexible poly(2-ethylhexyl acrylate) (P2EHA) block is first formed, and then, concomitantly, the poly(2-ethylhexyl acrylate)-b-poly(methyl acrylate)-b-poly(2-ethylhexyl acrylate) triblock polymer which becomes organized into micelles and the polymethyl acrylate (MeA) that forms the core of the particle; a flexible poly(methyl acrylate) particle stabilized by the said triblock is finally obtained in dispersion.

The weight ratio between, on the one hand, the monomers serving to form the soluble block(s) of the block stabilizing polymer, and, on the other hand, the monomers forming the core of the particle+ the monomers forming the insoluble block(s) of the stabilizing polymer, is preferably between 0.5/100 and 15/100 (i.e. 0.5 to 15 parts by weight of monomers serving to form the soluble blocks per 100 parts by weight of the monomers serving to form the insoluble blocks+ the core of the particle), especially between 1/100 and 10/100, or even between 1.5/100 and 8/100.

The dispersion of polymer particles according to the invention is very preferentially monodisperse, which means that it has a very small particle size polydispersity, especially less than or equal to 0.15 and preferably less than or equal to 0.12; the particle size polydispersity (PDI) may be determined especially by dynamic light scattering, using a Malvern Zetasizer Nano S90 machine; polystyrene cuvettes (1 cm×1 cm) are used and the measurements are taken at 20° C., on solutions comprising 1 drop of dispersion diluted in 1 ml of isododecane.

The polymer particles in dispersion according to the invention preferably have a spherical shape and a diameter greater than 100 nm, especially between 100 and 1000 nm, in particular between 125 and 800 nm and preferentially between 150 and 700 nm (determined by dynamic light scattering, using a Malvern Zetasizer Nano S90).

Preferably, the dispersion according to the invention has a solids content of from 5% to 40% by weight, especially from 6% to 30% by weight, or even from 7% to 25% by weight.

The dispersions according to the invention find a most particular application in cosmetics. Thus, they may be present in the cosmetic compositions according to the invention in an amount such that the amount of polymeric dry matter (or active material) in the composition represents 1% to 70% by weight, preferably 2% to 50% by weight, especially 5% to 40% by weight, or even 7% to 30% by weight, relative to the total weight of the composition.

The cosmetic compositions according to the invention also comprise a cosmetically acceptable medium, i.e. a medium that is compatible with keratin materials such as facial or bodily skin, the lips, the hair, the eyelashes, the eyebrows and the nails.

The composition may advantageously comprise a fatty phase, which may itself comprise oils and/or solvents that are preferably lipophilic, and also fatty substances that are solid at room temperature, such as waxes, pasty fatty substances and gums, and mixtures thereof.

Among the constituents of the fatty phase, mention may be made of volatile or non-volatile oils, which may be chosen from natural or synthetic carbon-based, hydrocarbon-based or fluoro oils, which are optionally branched, alone or as a mixture.

The term "non-volatile oil" means an oil that is capable of remaining on the skin at room temperature and atmospheric pressure for at least one hour and that especially has a non-zero vapour pressure at room temperature (25° C.) and atmospheric pressure, of less than 0.01 mmHg (1.33 Pa).

Mention may be made in particular of non-volatile carbon-based and especially hydrocarbon-based oils, of plant, mineral, animal or synthetic origin, such as liquid paraffin (or petroleum jelly), squalane, hydrogenated polyisobutene (Parleam), perhydrosqualene, mink oil, macadamia oil, turtle oil, soybean oil, sweet almond oil, beauty-leaf oil, palm oil, grape seed oil, sesame seed oil, corn oil, arara oil, rapeseed oil, sunflower oil, cottonseed oil, apricot oil, castor oil, avocado oil, jojoba oil, olive oil or cereal germ oil, and shea butter; linear, branched or cyclic esters containing more than 6 carbon atoms and especially 6 to carbon atoms, such as lanolic acid, oleic acid, lauric acid or stearic acid esters; esters derived from long-chain acids or alcohols (i.e. containing from 6 to carbon atoms), especially the esters of formula RCOOR' in which R represents a higher fatty acid residue containing from 7 to 19 carbon atoms and R' represents a hydrocarbon-based chain containing from 3 to 20 carbon atoms, in particular C12-C36 esters such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, bis(2-ethylhexyl) succinate, diisostearyl malate, and glyceryl or diglyceryl triisostearate; higher fatty acids, especially of C14-C22, such as myristic acid, palmitic acid, stearic acid, behenic acid, oleic acid, linoleic acid, linolenic acid or isostearic acid; higher fatty alcohols, especially of C16-C22, such as cetanol, oleyl alcohol, linoleyl alcohol, linolenyl alcohol, isostearyl alcohol or octyldodecanol; and mixtures thereof.

Mention may also be made of decanol, dodecanol, octadecanol, liquid triglycerides of fatty acids of 4 to 10 carbon atoms, for instance heptanoic or octanoic acid triglycerides, caprylic/capric acid triglycerides; linear or branched hydrocarbons, of mineral or synthetic origin, such as liquid paraffins and derivatives thereof, petroleum jelly, polydecenes and hydrogenated polyisobutene, such as Parleam; synthetic esters and ethers, especially of fatty acids, for instance, Purcellin oil, isopropyl myristate, 2-ethylhexyl palmitate, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and fatty alkyl heptanoates, octanoates and decanoates; polyol esters, for instance propylene glycol dioctanoate, neopentyl glycol diheptanoate or diethylene glycol diisononanoate; and pentaerythritol esters; fatty alcohols containing from 12 to 26 carbon atoms, for instance octyldodecanol, 2-butyloctanol, 2-hexyldecanol or 2-undecylpentadecanol.

Mention may also be made of ketones that are liquid at room temperature, such as methyl ethyl ketone, methyl isobutyl ketone, diisobutyl ketone, isophorone, cyclohexanone or acetone; propylene glycol ethers that are liquid at room temperature, such as propylene glycol monomethyl ether, propylene glycol monomethyl ether acetate or dipropylene glycol mono-n-butyl ether; short-chain esters (containing from 3 to 8 carbon atoms in total), such as ethyl acetate, methyl acetate, propyl acetate, n-butyl acetate or isopentyl acetate; ethers that are liquid at room temperature, such as diethyl ether, dimethyl ether or dichlorodiethyl ether; alkanes that are liquid at room temperature, such as decane, heptane, dodecane, isododecane, isohexadecane or cyclohexane; aromatic cyclic compounds that are liquid at room temperature, such as toluene and xylene; aldehydes that are liquid at room temperature, such as benzaldehyde and acetaldehyde, and mixtures thereof.

Among the volatile compounds, mention may be made of non-silicone volatile oils, especially C8-C16 isoparaffins, for instance isododecane, isodecane and isohexadecane. Mention may be made more preferentially of volatile or non-volatile alkanes that are liquid at room temperature, and more particularly decane, heptane, dodecane, isododecane, isohexadecane, cyclohexane and isodecane, and mixtures thereof.

The fatty phase may be present in a content ranging from 0.01% to 95%, preferably from 0.1% to 90%, more preferably from 10% to 85% and better still from 30% to 80% by weight relative to the total weight of the composition.

The composition may also comprise a hydrophilic phase comprising water or a mixture of water and of hydrophilic organic solvent(s), for instance alcohols and especially linear or branched lower monoalcohols containing from 2 to 5 carbon atoms, for instance ethanol, isopropanol or n-propanol, and polyols, for instance glycerol, diglycerol, propylene glycol, sorbitol, pentylene glycol, and polyethylene glycols, or alternatively hydrophilic $C_2$ ethers and hydrophilic $C_2$-$C_4$ aldehydes. Water or the mixture of water and of hydrophilic organic solvents may be present in the composition according to the invention in a content ranging from 0.1% to 80% by weight and preferably from 1% to 70% by weight relative to the total weight of the composition.

The composition according to the invention may also comprise waxes and/or gums. For the purposes of the present invention, the term "wax" means a lipophilic compound that is solid at room temperature (25° C.), with a reversible solid/liquid change of state, having a melting point of greater than or equal to 30° C., which may be up to 120° C. By bringing the wax to the liquid state (melting), it is possible to make it miscible with the oils that may be present and to form a microscopically homogeneous mixture, but on returning the temperature of the mixture to room temperature, recrystallization of the wax in the oils of the mixture is obtained. The melting point of the wax may be measured using a differential scanning calorimeter (DSC), for example the calorimeter sold under the name DSC 30 by the company Mettler.

The waxes may be hydrocarbon-based waxes, fluoro waxes and/or silicone waxes and may be of plant, mineral, animal and/or synthetic origin. In particular, the waxes have a melting point of greater than 25° C. and better still greater than 45° C. As wax that may be used in the composition of the invention, mention may be made of beeswax, carnauba wax or candelilla wax, paraffin, microcrystalline waxes, ceresin or ozokerite; synthetic waxes, for instance polyethylene waxes or Fischer Tropsch waxes, and silicone waxes, for instance alkyl or alkoxy dimethicones containing from 16 to 45 carbon atoms.

The gums are generally high molecular weight polydimethylsiloxanes (PDMSs) or cellulose or polysaccharide gums, and the pasty substances are generally hydrocarbon-based compounds, for instance lanolins and derivatives thereof, or alternatively PDMSs.

The nature and amount of the solid substances depend on the desired mechanical properties and textures. As a guide, the composition may contain from 0.01% to 50% by weight and better still from 1% to 30% by weight of waxes relative to the total weight of the composition.

The composition according to the invention may also comprise one or more dyestuffs chosen from water-soluble dyes, liposoluble dyes and pulverulent dyestuffs, for instance pigments, nacres and glitter flakes that are well known to those skilled in the art. The dyestuffs may be present in the composition in a content ranging from 0.01% to 50% by weight and preferably from 0.01% to 30% by weight relative to the weight of the composition.

The term "pigments" should be understood as meaning white or coloured, mineral or organic particles of any form, which are insoluble in physiological medium and are intended to colour the composition. The term "nacres" should be understood as meaning iridescent particles of any form, especially produced by certain molluscs in their shell or else synthesized. The pigments may be white or coloured, and mineral and/or organic. Among the mineral pigments that may be mentioned are titanium dioxide, optionally surface-treated, zirconium oxide or cerium oxide, and also zinc oxide, iron oxide (black, yellow or red) or chromium oxide, manganese violet, ultramarine blue, chromium hydrate and ferric blue, and metal powders, for instance aluminium powder or copper powder. Among the organic pigments that may be mentioned are carbon black, pigments of D & C type, and lakes based on cochineal carmine or on barium, strontium, calcium or aluminium. The nacreous pigments may be chosen from white nacreous pigments such as mica coated with titanium or with bismuth oxychloride, coloured nacreous pigments such as titanium mica coated with iron oxides, titanium mica coated especially with ferric blue or with chromium oxide, titanium mica coated with an organic pigment of the abovementioned type, and also nacreous pigments based on bismuth oxychloride.

Among the water-soluble dyes that may be mentioned are the disodium salt of ponceau, the disodium salt of alizarin green, quinoline yellow, the trisodium salt of amaranth, the disodium salt of tartrazine, the monosodium salt of rhodamine, the disodium salt of fuchsin, xanthophyll and methylene blue.

The composition according to the invention may also comprise one or more fillers, especially in a content ranging from 0.01% to 50% by weight and preferably ranging from 0.01% to 30% by weight relative to the total weight of the composition. The term "fillers" should be understood as meaning colourless or white, mineral or synthetic particles of any form, which are insoluble in the medium of the composition irrespective of the temperature at which the composition is manufactured. These fillers serve especially to modify the rheology or texture of the composition. The fillers may be mineral or organic of any form, plateletshaped, spherical or oblong, irrespective of the crystallographic form (for example lamellar, cubic, hexagonal, orthorhombic, etc.). Mention may be made of talc, mica, silica, kaolin, polyamide (Nylon®) powders (Orgasol® from Atochem), poly-β-alanine powders and polyethylene powders, powders of tetrafluoroethylene polymers (Teflon®), lauroyllysine, starch, boron nitride, hollow polymer microspheres such as those of polyvinylidene chloride/acrylonitrile, for instance Expancel® (Nobel Industrie) or of acrylic acid copolymers (Polytrap® from the company Dow Corning) and silicone resin microbeads (for example Tospearls® from Toshiba), elastomeric polyorganosiloxane particles, precipitated calcium carbonate, magnesium carbonate, magnesium hydrogen carbonate, hydroxyapatite, hollow silica microspheres (Silica Beads® from Maprecos), glass or ceramic microcapsules, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate.

The composition may also comprise an additional polymer such as a film-forming polymer. According to the present invention, the term "film-forming polymer" means a polymer that is capable, by itself or in the presence of an auxiliary film-forming agent, of forming a continuous film that adheres to a support and especially to keratin materials. Among the film-forming polymers that may be used in the composition of the present invention, mention may be made of synthetic polymers, of free-radical type or of polycondensate type, polymers of natural origin, and mixtures thereof, in particular acrylic polymers, polyurethanes, polyesters, polyamides, polyureas and cellulose-based polymers, for instance nitrocellulose.

The composition according to the invention may also comprise ingredients commonly used in cosmetics, such as vitamins, thickeners, gelling agents, trace elements, softeners, sequestrants, fragrances, acidifying or basifying agents, preserving agents, sunscreens, surfactants, antioxidants, hair-loss counteractants, antidandruff agents, propellants and ceramides, or mixtures thereof. Needless to say, a person skilled in the art will take care to select this or these optional additional compound(s), and/or the amount thereof, such that the advantageous properties of the composition according to the invention are not, or are not substantially, adversely affected by the envisaged addition.

The composition according to the invention may especially be in the form of a suspension, a dispersion, a solution, especially an organic solution, a gel, an emulsion, especially an oil-in-water (O/W) or water-in-oil (W/O) emulsion, or a multiple emulsion (W/O/W, polyol/O/W or O/W/O emulsion), or in the form of a cream, a paste, a mousse, a dispersion of vesicles, especially of ionic or nonionic lipids, a two-phase or multi-phase lotion, a spray, a powder or a stick (wand).

A person skilled in the art may select the appropriate galenical form, and also the method for preparing it, on the basis of his general knowledge, taking into account firstly the nature of the constituents used, especially their solubility in the support, and secondly the intended use of the composition.

The dispersions according to the invention are thus finally formed from flexible polymer particles, of monodisperse size and of fairly large diameter (preferably greater than 100 nm), and lead to flexible, comfortable, glossy film-forming deposits, at the observation temperature (25° C.), which are advantageous especially for makeup, hair dyeing, hair conditioning, skincare and/or antisun applications.

Furthermore, since the said dispersion is in oily medium, it becomes easy to formulate it in oily-medium-based cosmetic compositions commonly used in cosmetics, in particular anhydrous media.

The composition according to the invention may be a makeup composition, especially a complexion product such as a foundation, a face powder or an eyeshadow; a lip product such as a lipstick, a lipcare product or a lip gloss; a concealer product; a blusher, a mascara or an eyeliner; an eyebrow makeup product, a lip pencil or an eye pencil; a nail product such as a nail varnish or a nailcare product; a body makeup product; a hair makeup product (hair mascara or hair lacquer).

The composition according to the invention may be a composition for protecting or caring for the skin of the face, the neck, the hands or the body, especially an antiwrinkle composition, an anti-fatigue composition for making the skin look radiant, or a moisturizing or medicated composition; an antisun or self-tanning composition.

The composition according to the invention may also be a hair product, especially for holding the hairstyle or for shaping the hair; for caring for, conditioning or hygiene of the hair or even for dyeing the hair. The hair compositions are preferably shampoos, hair conditioners, hairsetting gels or lotions, blow-waving lotions, or fixing and styling compositions such as lacquers or sprays. The lotions may be conditioned in various forms, especially in vaporizers or pump-dispenser bottles or in aerosol containers in order to apply the composition in vaporized form or in the form of a mousse. Such conditioning forms are indicated, for example, when it is desired to obtain a spray or a mousse for fixing or treating the hair.

The composition according to the invention finds a most particular application as a makeup composition, especially a lipstick, lip gloss, eyeshadow, face powder, nail varnish or nailcare product, and also as a haircare product.

A subject of the invention is also a cosmetic process for making up, cleansing, sun-protecting, shaping, dyeing or caring for keratin materials, especially bodily or facial skin, the lips, the nails, the hair and/or the eyelashes, comprising the application to the said materials of a cosmetic composition as defined previously.

The invention is illustrated in greater detail in the examples that follow, which are given as illustrations.

EXAMPLE 1

Preparation of Dispersion D1

A/

30 g (4.78 mol/l) of 2-ethylhexyl acrylate, $4.6 \times 10^{-3}$ mol/l of initiator (Trigonox 21S from Akzo) and $4.4 \times 10^{-2}$ mol/l of control agent (TTC or S,S-bis[1-(2-ethylhexyloxycarbonyl)ethyl]trithiocarbonate) are mixed together in a 100 ml three-necked round-bottomed flask connected to a condenser equipped with a bubbler.

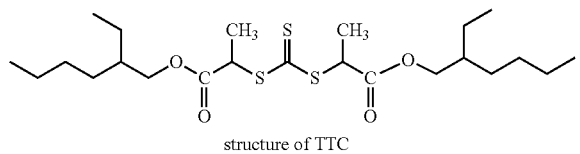 [SMILES: CCCCC(CC)COC(=O)C(C)SC(=S)SC(C)C(=O)OCC(CC)CCCC]

structure of TTC

The flask is stoppered and the oxygen is then stripped out by bubbling with nitrogen for 30 minutes. The flask is then placed in an oil bath thermostatically regulated at 60° C., with stirring from 250 to 300 rpm. The reaction is stopped after 5 hours. The polymer is precipitated twice from cold methanol and then dried under reduced pressure for 24 hours at 25° C.

The final characteristics of the polymer are given below:

| Degree of conversion (%) | $Mn^{PS}$* | Ip | $Mn^{LS}$* | DP**** |
|---|---|---|---|---|
| 89 | 16 400 | 1.08 | 19 200 | 102 |

*$Mn^{PS}$: number-average molar mass determined by GPC with polystyrene calibration
**Ip = Mw/Mn; Mw and Mn being the weight-average and number-average molar masses, determined by GPC with polystyrene calibration ($Mn^{PS}$ and $Mw^{PS}$)
***$Mn^{LS}$: number-average molar mass, determined by GPC with detection by light scattering.
****DP: degree of polymerization, determined from the $Mn^{LS}$

B/

The following are placed in a 100 ml three-necked flask:
2.0 mol/l of methyl acrylate (2 mol per litre of isododecane),
polymer prepared above, in an amount such that the weight ratio of polymer prepared above/methyl acrylate is 1.5/100,
$1.33 \times 10^{-3}$ mol/l of initiator (Trigonox 21S from Akzo),
isododecane so as to obtain a solids content of 22.3% by weight.

Nitrogen is bubbled through the reaction mixture for 30 minutes, with stirring; the mixture is then immersed in an oil bath preheated to 80° C., with stirring at 250 rpm. The appearance of cloudiness corresponds to the start of the reaction. The flask is removed after 4 hours of reaction, and placed in cold water to stop the reaction.

A dispersion, in isododecane, of polymethyl acrylate stabilized with a poly(2-ethylhexyl acrylate)-b-polymethyl acrylate-b-poly(2-ethylhexyl acrylate) triblock polymer is finally obtained, the characteristics of which polymer are as follows:

| Degree of conversion (%) | Solids content | Diameter[b] (nm) | PDI[c] |
|---|---|---|---|
| 77% | 17% | 319 | 0.03 |

[b]mean diameter determined by dynamic light scattering (Malvern Zetasizer Nano S90)
[c]particle size polydispersity index.

EXAMPLE 2

Preparation of Dispersion D2

The following are placed in a 250 ml three-necked flask:
2.01 mol/l of methyl acrylate (2.01 mol per litre of isododecane),
polymer prepared in step A of Example 1 above, with a polymer/methyl acrylate weight ratio of 3.01/100,
$1.53 \times 10^{-3}$ mol/l of initiator (Trigonox 21S from Akzo),
isododecane so as to obtain a solids content of 22.7% by weight.

Nitrogen is bubbled through the reaction mixture for 30 minutes, with stirring; the mixture is then immersed in an oil bath preheated to 80° C., with stirring at 250 rpm. The appearance of cloudiness corresponds to the start of the reaction. The flask is removed after 6 hours of reaction, and placed in cold water to stop the reaction.

A dispersion, in isododecane, of polymethyl acrylate stabilized with a poly(2-ethylhexyl acrylate)-b-polymethyl acrylate-b-poly(2-ethylhexyl acrylate) triblock polymer is finally obtained, the characteristics of which are as follows:

| Degree of conversion (%) | Solids content | Diameter[b] (nm) | PDI[c] |
|---|---|---|---|
| 94% | 21% | 212 | 0.02 |

By DMTA, only one Tg is observed for the dispersion (Tg=38° C.), corresponding to that of PMeA; the low Tg (~−50° C. in theory) of the P2EHA part is not detected.

DMTA was performed after 6 days of drying (25° C. and 45% RH) of films with a final thickness of about 250 µm.
Machine: DMA 2980 (TA Instruments)
DMTA: from −100 to +200° C. at 3° C./min
No tack is detected in the final film.

EXAMPLE 3

Preparation of Dispersion D3

The following are placed in a 250 ml three-necked flask:
2.0 mol/l of methyl acrylate (2.0 mol per litre of isododecane),
polymer prepared in step A of Example 1 above, with a polymer/methyl acrylate weight ratio of 6.05/100,
$1.23 \times 10^{-3}$ mol/l of initiator (Trigonox 21S from Akzo),
isododecane so as to obtain a solids content of 23.2% by weight.

Nitrogen is bubbled through the reaction mixture for 30 minutes, with stirring; the mixture is then immersed in an oil bath preheated to 80° C., with stirring at 250 rpm. The appearance of cloudiness corresponds to the start of the reaction. The flask is removed after 6 hours of reaction, and placed in cold water to stop the reaction.

A dispersion, in isododecane, of polymethyl acrylate stabilized with a poly(2-ethylhexyl acrylate)-b-polymethyl acrylate-b-poly(2-ethylhexyl acrylate) triblock polymer is finally obtained, the characteristics of which are as follows:

| Degree of conversion (%) | Solids content | Diameter[b] (nm) | PDI[c] |
|---|---|---|---|
| 97% | 23% | 117 | 0.03 |

By DMTA, only one Tg is observed for the dispersion (Tg=36° C.)
No tack is detected in the final film.

EXAMPLE 4

Preparation of Dispersion D4

The following are placed in a 250 ml three-necked flask:
1.93 mol/l of methyl acrylate (1.93 mol per litre of isododecane),
polymer prepared in step A of Example 1 above, with a polymer/methyl acrylate weight ratio of 2.93/100,
$1.51 \times 10^{-3}$ mol/l of initiator (Trigonox 21S from Akzo),
isododecane so as to obtain a solids content of 22.3% by weight.

Nitrogen is bubbled through the reaction mixture for 30 minutes, with stirring; the mixture is then immersed in an oil bath preheated to 80° C., with stirring at 250 rpm. The appearance of cloudiness corresponds to the start of the reaction. After 1 hour 10 minutes of reaction, 1 mol % of crosslinking agent, relative to the methyl acrylate (EGDMA: ethylene glycol dimethacrylate), is added, and the reaction is continued. The flask is removed after 6 hours of reaction in total, and placed in cold water to stop the reaction.

A dispersion, in isododecane, of polymethyl acrylate stabilized with a poly(2-ethylhexyl acrylate)-b-polymethyl acrylate-b-poly(2-ethylhexyl acrylate) triblock polymer is finally obtained, the characteristics of which are as follows:

| Degree of conversion (%) | Solids content | Diameter[b] (nm) | PDI[c] |
|---|---|---|---|
| 91% | About 20% | 208 | 0.02 |

By DMTA, only one Tg is observed for the dispersion (Tg=39° C.)
No tack is detected in the final film.

EXAMPLE 5

Preparation of the Comparative Dispersion (Outside the Invention)

600 g of isododecane and 230 g of heptane are placed in a reactor, followed by introduction of a shower of 30 g of Kraton G1701E (styrene/isoprene block copolymer) with stirring. After 30 minutes of stirring, 50 g of methyl acrylate, 10 g of acrylic acid and 3 g of initiator (Trigonox 21S) are added. The reaction medium is maintained at 90° C. for 45 minutes; blanching is noted immediately on reaching 90° C., with exothermicity of 10° C. At the end of the exothermicity (about 15 minutes after blanching), 140 g of methyl acrylate and 2.2 g of initiator (Trigonox 21S) are added over 1 hour at 90° C. The mixture is left for 3 hours at 90° C., and the heptane is then distilled off and replaced with 200 g of isododecane.

A dispersion of methyl acrylate and acrylic acid particles, surface-stabilized with a styrene/isoprene block copolymer, in isododecane is obtained.

EXAMPLE 6

Characterization of the Dispersions

The gloss is measured and the tack is compared the presence of sebum or olive oil, for dispersions D2, D3 and D4 of the invention relative to the prior-art dispersion, which is itself glossy and shows good remanence and resistance to attack (oil, sebum), but which is stabilized with a polymer that is non-covalently bonded by means of physical interactions to the polymer particles, as described in EP 749 747.
Gloss Measured Using a Glossmeter on a Dry Deposit of Polymer The gloss is measured using a glossmeter, in a conventional manner via the following method: a coat 200 µm thick of a 50% dispersion of the polymer in isododecane is spread onto a Leneta contrast card of reference Form 1A Penopac, using an automatic spreader. The coat covers at least the black background of the card. The deposit is left to dry for 24 hours at a temperature of 25° C., and the gloss at 20° is then measured on the black background using a Dr Lange glossmeter, REF03. A measurement at 20° higher than about 50 gives a gloss considered as being acceptable, and very satisfactory if the measurement is higher than 60.

The following results are obtained:

|  | D2 | D3 | D4 | comparative |
|---|---|---|---|---|
| Gloss 20° | 50 | 62 | 62 | 52 |

Tack

The sensitivity of the films to sebum and to olive oil was evaluated sensorily, in the following manner: a film about 20 µm thick is deposited on a flat surface, using a dispersion containing 50% polymer solids, and is left to dry for 3 days at 25° C.; 1 drop of sebum or 1 drop of olive oil is then placed on the film, it is left in contact for 5 minutes or 1 hour, and the tack of the film is then assessed comparatively, by finger.

The following results are obtained:

|  | D2 | D3 | D4 |
|---|---|---|---|
| Olive oil tack after 5 minutes | Identical to the comparative | Identical to the comparative | Identical to the comparative |
| Sebum tack after 5 minutes | Identical to the comparative | Identical to the comparative | Identical to the comparative |
| Olive oil tack after 1 hour | Identical to the comparative | Identical to the comparative | Identical to the comparative |
| Sebum tack after 1 hour | Identical to the comparative | Identical to the comparative | Identical to the comparative |

It is found that the dispersions according to the invention give films that are at least as glossy as, or even glossier than, those obtained with the prior art; the films according to the invention do not develop any tack in the presence of olive oil or liquid sebum, whether after 5 minutes or 1 hour of contact.

It may moreover be thought that the dispersions according to the invention will be more stable over time than that of the prior art.

EXAMPLE 7

Mascara Composition

A mascara having the following composition is prepared:

| | |
|---|---|
| Modified hectorite (Bentone ® 38 V from Elementis) | 2 g |
| Pigments | 2 g |
| Dispersion D1 | 15 g DM* |
| Isododecane | qs 100 g |

*DM: dry matter

EXAMPLE 8

Lipstick Wand

The following lipstick composition is prepared (weight %):

| | |
|---|---|
| Polyethylene wax | 3% |
| Dispersion D2 | 13% DM |
| Isododecane | qs 100% |

The composition obtained has good cosmetic properties.

EXAMPLE 9

Lip Gloss

A gloss having the following composition is prepared (weight %):

| | |
|---|---|
| Dispersion D3 | 5% DM |
| Parleam | qs 100% |

The composition obtained has good cosmetic properties.

EXAMPLE 10

W/O Foundation

A foundation composition comprising the following compounds is prepared:

Phase A

| | |
|---|---|
| Cetyl Dimethicone copolyol (Abil EM 90 from the company Goldschmidt) | 3% |
| Diglyceryl isostearyl succinate (Imwitor 780K from the company Condea) | 0.6% |
| Pigments (hydrophobic iron oxides and titanium oxides) | 1% |
| Dispersion D3 | 20% (i.e. 1.3% DM) |
| Isododecane | qs 100 g (on phase A) |

Phase B

| | |
|---|---|
| Magnesium sulfate | 0.7 g |
| Preserving agents | qs |
| Water | qs 100 g (on phase B) |

The composition obtained has good cosmetic properties.

EXAMPLE 11

Nail Varnish

A nail varnish having the following composition is prepared:

| | |
|---|---|
| Dispersion D1 | 4 g of DM |
| Butyl acetate | 25 g |
| Isopropanol | 11 g |
| Hexylene glycol | 2.5 g |
| Pigment | 1 g |
| Modified hectorite (Bentone ® 27 V from Elementis) | 1.3 g |
| Ethyl acetate | qs 100 g |

This varnish was judged as having very good cosmetic properties.

EXAMPLE 12

Powder

A compact powder having the following composition is prepared:

Composition A:

| | |
|---|---|
| Talc | 10 g |
| Bismuth oxychloride | 10 g |
| Zinc stearate | 4 g |
| Dispersion D2 | 5 g DM |

Composition B:

| | |
|---|---|
| Iron oxides | 2 g |
| Liquid petroleum jelly | 6 g |

The powder is obtained in the following manner: composition A is ground in a Kenwood mill for about 5 minutes with gentle stirring, composition B is added, and the mixture is ground for about 2 minutes at the same speed, and then for 3 minutes at a higher speed. The preparation is then screened through a 0.16 mm screen, and this mixture is then compacted in dishes. A compact powder with good cosmetic properties is obtained.

EXAMPLE 13

Facial Gel

The following composition is prepared:

| | |
|---|---|
| isopropyl palmitate | 10 g |
| modified hectorite | 0.15 g |
| oxyethylenated (40 OE) sorbitan heptaoleate | 5 g |
| dispersion D2 | 9 g DM |
| Parleam | qs 100 g |

A gel with good cosmetic properties is obtained.

EXAMPLE 14

Care Oil

The following composition is prepared:

| dispersion D2 | 12 g DM |
|---|---|
| jojoba oil | 10 g |
| soybean oil | 10 g |

A care oil that can be applied to the body or the face is obtained.

The invention claimed is:

1. A dispersion of polymer particles, comprising:
a liquid carbon-based medium, and
particles having a flexible polymeric core and being surface-stabilized with a block stabilizing polymer in the form of micelles such that the block stabilizing polymer is adsorbed onto the particles and produced by a process comprising preparing the block stabilizing polymer by polymerization and adding that prepared block stabilizing polymer to one or more monomers forming the flexible polymeric core of the particles and polymerizing the one or more monomers forming the flexible polymeric core of the particles in the presence of the block stabilizing polymer,
wherein the block stabilizing polymer comprises at least one block that is soluble in the carbon-based medium and at least one block that is insoluble in the carbon-based medium, the insoluble block comprises 50 wt % to 100 wt % of at least one insoluble monomer in the medium, selected from the group of monomers, and salts thereof consisting of:
(i) (meth)acrylates of formula: $CH_2=C(CH_3)-COOR'_1$ or $CH_2=CH-COOR'_1$ in which $R'_1$ is one selected from the group consisting of:
a linear or branched alkyl group containing from 1 to 6 carbon atoms, optionally comprising in its chain one or more heteroatoms selected from the group consisting of O, N and S; and/or optionally comprising one or more substituents selected from the group consisting of —OH, halogen atoms and —NR'R" wherein R' and R", are independently linear or branched C1-C4 alkyls; optionally substituted with at least one polyoxyalkylene group comprising a repetition of from 5 to 30 oxyalkylene units; with the proviso that tert-butyl methacrylate and isobutyl acrylate are excluded from this definition;
a cyclic alkyl group containing from 3 to 6 carbon atoms, optionally comprising in its chain one or more heteroatoms chosen from O, N and S and/or possibly comprising one or more substituents selected from the group consisting of OH and halogen atoms;
(ii) (meth)acrylamides of formula: $CH_2=C(CH_3)-CONR'_3R)$ or $CH_2=CH-CONR'_3R'_4$,
wherein:
$R'_3$ and $R'_4$, are independently a hydrogen atom or a linear or branched alkyl group containing from 1 to 6 carbon atoms, optionally comprising one or more substituents selected from the group consisting of —OH, halogen atoms and —NR'R" wherein R' and R", are each independently linear or branched C1-C4 alkyls; or
$R'_3$ represents a hydrogen atom and $R'_4$ represents a 1,1-dimethyl-3-oxobutyl group;
(iii) ethylenically unsaturated monomer(s) comprising at least one carboxylic, phosphoric or sulfonic acid function, and salts thereof;
(iv) vinyl esters of formula $R'_6-COO-CH=CH_2$ wherein $R'_6$ is a linear or branched alkyl group containing from 1 to 6 atoms or a cyclic alkyl group containing from 3 to 6 carbon atoms and/or an aromatic group;
(v) ethylenically unsaturated monomers comprising at least one tertiary amine function;
(vi) di-n-alkylitaconates of formula $CH_2=C(CH_2-COO(CH_2)_{n-1}-CH_3)-COO(CH_2)_{n-1}-CH_3$, wherein n is an integer from 0 to 4;
(vii) ethylenic monomers having an ester group which contains silanes, silsesquioxanes, siloxanes or carbosiloxane dendrimers, with the exception of monomers containing only one silicon atom; and
(viii) polydimethylsiloxane (PDMS)—"emulsion" macromonomers selected from the group consisting of polydimethylsiloxanes containing monoacryloyloxy or monomethacryloyloxy end group, and monomers of following formula:

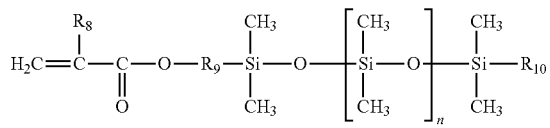

wherein
$R_8$ is a hydrogen atom or a methyl group;
$R_9$ is a linear or branched, divalent hydrocarbon-based group containing from 1 to 10 carbon atoms and optionally containing one or two ether bonds —O—;
$R_{10}$ is a linear or branched alkyl group containing from 1 to 10 carbon atoms;
n is an integer ranging from 1 to 300.

2. The dispersion according to claim 1, wherein the particles with a flexible polymeric core are obtained by polymerization of monomers, alone or as a mixture, chosen such that the glass transition temperature (Tg) of the resulting polymer, forming the flexible core, is less than 20° C.

3. The dispersion according to claim 2, wherein the particles with a flexible polymeric core is obtained by polymerization of monomers, comprising 60% to 100% by weight, relative to a total weight of monomers, of at least one monomer whose homopolymer has a Tg less than 20° C.; and optionally from 0.1% to 40% by weight of monomers whose homopolymer has a Tg of greater than or equal to 20° C.

4. The dispersion according to claim 3, wherein the monomers having a homopolymer with a Tg less than 20° C. comprise at least one selected from the group of monomers, and salts thereof consisting of:
(meth)acrylates of formula $CH_2=C(CH_3)-COOR$ or $CH_2=CH-COOR$, wherein R represents a linear, branched or cyclic, saturated or unsaturated, alkyl group or aromatic group, comprising 1 to 32 carbon atoms, optionally having one or more substituents selected from the group consisting of —OH, halogen atoms and —NR'R" wherein R' and R", are each, independently, a or branched C1-C4 alkyls optionally interrupted with an oxygen atom; and
ethylenic monomers having an ester group comprising one selected from the group consisting of silanes, silsesquioxanes, siloxanes and carbosiloxane dendrimers, with the exception of monomers containing only one silicon atom.

5. The dispersion according to claim 1, wherein the block stabilizing polymer comprises three blocks (triblock).

6. The dispersion according to claim 1, wherein the soluble block of the block stabilizing polymer comprises 50% to 100% by weight of at least one monomer soluble in the medium, selected from the group of monomers consisting of:
methacrylates of formula $CH_2$=$C(CH_3)$—$COOR_1$
wherein $R_1$ is a linear or branched C8-C22 alkyl group; a cyclic alkyl group containing 8 to 30 carbon atoms; or a tert-butyl group;
the acrylates of formula $CH_2$=$CH$—$COOR_2$
wherein $R_2$ is a linear or branched C8-C22 alkyl group; a cyclic alkyl group containing 8 to 30 carbon atoms; or an isobutyl group;
(meth)acrylamides of formula $CH_2$=$C(CH_3)$—$CONR_3R_4$ or $CH_2$=$CH$—$CONR_3R_4$, wherein $R_3$ is a hydrogen atom or a linear or branched C1-C12 alkyl group and $R_4$ is a linear or branched $C_8$ to $C_{12}$ alkyl group;
di-n-alkylitaconates of formula $CH_2$=$C(CH_2$—$COO(CH_2)_{n-1}$—$CH_3)$—$COO(CH_2)_{n-1}$—$CH_3$, wherein n is an integer greater than or equal to 5;
vinyl esters of formula $R_5$—$CO$—$O$—$CH$=$CH_2$ wherein $R_5$ is a linear or branched $C_8$ to $C_{22}$ alkyl group;
ethers of vinyl alcohol and of an alcohol of formula $R_6O$—$CH$=$CH_2$ wherein $R_6$ is a linear or branched alkyl group containing from 8 to 22 carbon atoms;
ethylenic monomers having an ester group contains silanes or siloxanes, and which contain only one silicon atom such as (meth)acryloxypropyltrimethoxysilane; and
carbon-based macromonomers with a polymerizable end group.

7. The dispersion according to claim 1, wherein the insoluble block of the block stabilizing polymer comprises 50% to 100% by weight of at least one monomer that is insoluble in the said medium, selected from the group of monomers, and salts thereof consisting of:
(meth)acrylates of formula: $CH_2$=$C(CH_3)$—$COOR'_1$ or $CH_2$=$CH$—$COOR'_1$;
wherein $R'_1$ is a linear or branched alkyl group comprising from 1 to 6 carbon atoms, optionally comprising in its chain one or more heteroatoms selected from the group consisting of —O; N and S; and/or optionally comprising one or more substituents selected from the group consisting of —OH, halogen atoms and —NR'R" wherein R' and R" are, each independently, linear or branched C1-C4 alkyls;
ethylenically unsaturated monomers comprising at least one carboxylic acid function, and salts thereof;
ethylenic monomers having an ester group selected from the group consisting of silanes; and
polydimethylsiloxanes containing a monoacryloyloxy or monomethacryloyloxy end group, having the following formula:

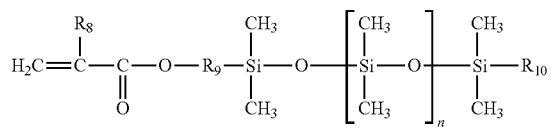

wherein:
$R_8$ is a hydrogen atom or a methyl group;
$R_9$ is a linear or branched, divalent hydrocarbon-based group containing from 1 to 10 carbon atoms and optionally containing one or two ether bonds —O—;
$R_{10}$ is a linear or branched alkyl group containing from 1 to 10 carbon atoms; and
n is an integer ranging from 1 to 300.

8. The dispersion according to claim 1, wherein the liquid carbon-based medium comprises at least 50% by weight, relative to the total weight of the carbon-based medium, of a carbon-based compound that is liquid at 25° C., with a global solubility parameter in a Hansen solubility space of less than or equal to 20 $(MPa)^{1/2}$, or a mixture of such compounds.

9. The dispersion according to claim 1, wherein the liquid carbon-based medium comprises at least one carbon-based compound selected from the group consisting of:
plant oils formed from fatty acid esters of polyols,
esters of formula RCOOR' wherein R represents a higher fatty acid residue comprising 7 to 19 carbon atoms and R' represents a hydrocarbon-based chain comprising from 3 to 20 carbon atoms,
volatile or non-volatile, linear or branched C8-C60 alkanes;
volatile or non-volatile, non-aromatic cyclic C5-C12 alkanes;
ethers containing 7 to 30 carbon atoms;
ketones containing 8 to 30 carbon atoms;
aliphatic fatty monoalcohols containing 12 to 30 carbon atoms, with the proviso that the hydrocarbon-based chain does not comprise any substitution groups; and
mixtures thereof.

10. The dispersion according to claim 1, wherein the liquid carbon-based medium comprises at least one selected from the group consisting of isopropyl myristate, octyldodecanol, a C5-C60 isoparaffin, isododecane, isohexadecane, isononyl isononanoate, and Parleam.

11. The dispersion according to claim 1, wherein a solids content is 5% to 40% by weight.

12. A cosmetic composition comprising, in a cosmetically acceptable medium, at least one dispersion according to claim 1.

13. The composition according to claim 12, wherein an amount of polymer solids in the composition is 1% to 70% by weight, relative to the total weight of the composition.

14. The composition according to claim 12, further comprising at least one ingredient selected from the group consisting of oils, solvents, fatty substances that are solid at room temperature, pasty fatty substances and gums; water; dyestuffs; fillers; additional polymers; vitamins, thickeners, gelling agents, trace elements, softeners, sequestrants, fragrances, acidifying or basifying agents, preserving agents, sunscreens, surfactants, antioxidants, hair-loss counteractants, antidandruff agents, propellants and ceramides.

15. The composition according to claim 12 wherein the composition is a makeup composition selected from the group consisting of a foundation, a face powder, an eyeshadow, a lipstick, a lipcare product, a lip gloss, a concealer product, a blusher, a mascara, an eyeliner, an eyebrow makeup product, a lip pencil, an eye pencil, a nail varnish, a nailcare product, a body makeup product, a hair makeup product, a composition for protecting or caring for the skin of the face, the neck, the hands or the body, an anti-fatigue composition for giving the skin radiance, a moisturizing or medicated composition, an anti sun or self-tanning composition, and a hair product for holding a hairstyle, for shaping hair; for hair care, conditioning or hygiene and for dyeing hair.

16. A cosmetic treatment process, comprising applying the cosmetic composition according to claim 12 to body or facial skin, lips, nails, hair and/or eyelashes, wherein the process is for making up, cleansing, sun-protecting, shaping, dyeing or caring for the area to which it is applied.

17. The dispersion according to claim 1, wherein the stabilizing polymer is adsorbed as a micelle.

18. The dispersion according to claim 1, wherein the particles are not crosslinked.

* * * * *

UNITED STATES PATENT AND TRADEMARK OFFICE
CERTIFICATE OF CORRECTION

PATENT NO. : 10,745,582 B2
APPLICATION NO. : 13/120437
DATED : August 18, 2020
INVENTOR(S) : Celine Farcet et al.

It is certified that error appears in the above-identified patent and that said Letters Patent is hereby corrected as shown below:

On the Title Page

Column 2, item (57), Under Other Publications, Line 1, "Properites, Theremal" should read --Properties, Thermal--.

In the Claims

Column 27, Line 58, Claim 1, "CONR'$_3$R)" should read --CONR'$_3$ R'$_4$--.

Column 28, Line 64, Claim 4, delete "a" and insert --linear--.

Column 29, Line 48, Claim 7, delete "O;" and insert --O,--.

Signed and Sealed this
Twenty-second Day of December, 2020

Andrei Iancu
*Director of the United States Patent and Trademark Office*